United States Patent [19]

Bollish

[11] Patent Number: 4,767,399
[45] Date of Patent: Aug. 30, 1988

[54] VOLUMETRIC FLUID WITHDRAWAL SYSTEM

[75] Inventor: Stephen J. Bollish, San Diego, Calif.

[73] Assignee: Fisher Scientific Group Inc. dba IMED Corporation, San Diego, Calif.

[21] Appl. No.: 938,622

[22] Filed: Dec. 5, 1986

[51] Int. Cl.$^4$ ............................................. A61M 37/00
[52] U.S. Cl. ............................................. 604/5; 604/6; 604/28; 210/646; 210/651; 210/416.1; 210/929
[58] Field of Search ........................................ 604/4–6, 604/28, 29, 151, 152; 210/645–647, 416.1, 929, 651

[56] References Cited

U.S. PATENT DOCUMENTS

| | | | |
|---|---|---|---|
| Re. 31,688 | 9/1984 | Popovich et al. | 604/6 |
| 2,061,399 | 11/1936 | Gross | 128/214 |
| 3,701,350 | 10/1972 | Guenther | 128/214 B |
| 3,902,490 | 9/1975 | Jacobsen et al. | 604/5 |
| 4,041,944 | 8/1977 | Rhodes | 128/214 B |
| 4,093,545 | 6/1978 | Cullis | 210/929 |
| 4,197,196 | 4/1980 | Pinkerton | 210/416.1 |
| 4,375,415 | 3/1983 | Lavender | 210/651 |
| 4,437,469 | 3/1984 | Djordjevich et al. | 128/672 |
| 4,449,539 | 5/1984 | Sarstedt | 128/764 |
| 4,457,747 | 7/1984 | Tu | 604/4 |
| 4,464,164 | 8/1984 | Troutner et al. | 604/5 |
| 4,466,804 | 8/1984 | Hino | 604/4 |
| 4,509,534 | 4/1985 | Tassin, Jr. | 128/764 |
| 4,512,763 | 4/1985 | Schneider | 604/5 |

FOREIGN PATENT DOCUMENTS 0033017 4/1981 Japan ..................................... 604/4

OTHER PUBLICATIONS

"The Practical Technical Aspects of Slow Continuous Ultrafiltration (SCUF) and Continuous Arteriovenous Hemofiltration (CAVH)" by S. Swann and E. Paganini, The Cleveland Clinic Foundation, (no date).
"Continuous Slow Ultrafiltration in Oliguric Acute Renal Failure" by E. P. Paganini and S. Nakamoto, Vol. XXVI Trans Am Soc Artifi Intern Organs, 1980.
"Intensive Care Potential of Continuous Arteriovenous Hemofiltration" by P. Kramer et al., Vol. XXVIII Trans Am Soc Artif Intern Organs 1982.
"Continuous Arteriovenous Hemofiltration" by Andre A. Kaplan, M.D. et al., Annals of Internal Medicine 1984.
"Technical Manual CADD-PCA Model 5200 Computerized Ambulatory Drug Delivery" by Pharmacia, Inc., Apr. 1985.
"Hemofiltration: A New Technique in Critical Care Nursing" by Chris Winkelman, R.N., Heart and Lung, May 1985, vol. 14, No. 3.
"Continuous Ultrafiltration–A New ICU Procedure for the Treatment of Fluid Overload" by Virginia Williams, R.N. et al., Critical Care Nurse, Jul./Aug. 1984.
"Mass Transfer in Arteriovenous Hemofiltration" by M. J. Lysaght et al., Arteriovenous Hemofiltration–A Kidney Replacement Therapy for the Intensive Care Unit printed in Germany by Springer-Verlag Berlin Heidleberg, 1985.
"Reducing Fluid Overload Without Hemodialysis" by Nancy Kadas, R.N., May 1986.

(List continued on next page.)

Primary Examiner—C. Fred Rosenbaum
Assistant Examiner—Mario Costantino
Attorney, Agent, or Firm—Workman, Nydegger & Jensen

[57] ABSTRACT

A system for withdrawing a predetermined volume of fluid from a patient comprises a filter assembly which is connected in line for fluid communication between an artery and a vein of the patient. A pump having a fluid chamber is connected in fluid communication with a filtrate port of the filter. Operation of the pump causes the withdrawal of fluid from the filter and into the pump chamber at a preselected volumetric rate. Periodically, the pump is cycled to expel the withdrawn fluid from the pump chamber. The system further comprises a fluid collection device for collecting the expelled fluids and may include means for replenishing fluids to the patient.

11 Claims, 2 Drawing Sheets

OTHER PUBLICATIONS

"Nursing Management of Continuous Arteriovenous Hemofiltration for Acute Renal Failure" by Joyce Cotton Palmer et al., Focus on Critical Care, Vol. 13, No. 5, Oct., 1986.

"Continuous Arteriovenous Hemofiltration in Acute Renal Failure" by Thomas A. Golper, M.D., American Journal of Kidney Diseases, Vol. VI, No. 6, Dec., 1985.

"Preventing Complications in Continuous Arteriovenous Hemofiltration" by Alice A. Whittaker, R.N. et al., Dimensions of Critical Care Nursing, Vol. 5, No. 2, Mar./Apr. 1986.

"Business Development Proposal–Volumetric Fluid Withdrawal Pump for CAVH and Related Procedures" by Steve Bollish, Clinical Services, Oct. 31, 1986.

"Hemofiltration arterioveineuse continue dans l'insuffisance renale aigue. Interet de la regulation du debit d'ultrafiltration" by T. Milcent et al., Nephrologie, 6, 1985.

VOLUMETRIC FLUID WITHDRAWAL SYSTEM

BACKGROUND

The present invention relates to systems and equipment sets used for the withdrawal of fluids from a patient. More particularly, the present invention relates to a system which disposes of body fluids containing waste products in the form of solutes. The present invention is particularly, but not exclusively, useful in the health care field for continuous arteriovenous hemofiltration.

DESCRIPTION OF THE PRIOR ART

The need to remove excess fluid or fluid containing dissolved waste products from selected patients has been long recognized. It is well known that certain conditions cause the build up of waste products within the body's blood system that necessitates their removal prior to the onset of further complications. Further, it is well known that the removal of dissolved waste products from the body's blood system can be accomplished through at least two well known procedures. These procedures are hemodialysis and continuous arteriovenous hemofiltration (CAVH).

The basic difference between hemodialysis and CAVH is quite elementary. On the one hand, hemodialysis performs selective removal of solutes, such as creatinine, blood-urea-nitrogen (BUN) and potassium from the blood system. On the other hand, CAVH is nonselective in its removal of these solutes from the blood system. More specifically, in hemodialysis blood is passed through a filter which is surrounded by a dialysate. Through the process of diffusion, the solutes dissolved within the blood pass through the membrane of the filter and diffuse into the dialysate. Thus, with hemodialysis there is little, if any, loss of fluid volume during the process. Unlike hemodialysis, CAVH operates on the principle that the removal of a given volume of fluids containing solutes proportionately decreases the amount of solutes in the blood system. This removal, however, obviously requires a fluid volume bulk replacement. Though this need for fluid replacement is not disadvantageous, it cannot be overlooked in the set up of a CAVH system and must be considered in order to maintain proper patient fluid balance.

The present invention is concerned with a CAVH type system. As previously implied, such systems are well known in the pertinent art and have been variously described in the appropriate literature. For instance, the article: American Journal of Kidney Diseases VI, December 1985, entitled *Continuous Arteriovenous Hemofiltration in Acute Renal Failure,* by T. A. Golper describes the basic elements and functioning of a CAVH system. Necessary for such a system is the incorporation of a hemofilter for filtering the unwanted solutes from the blood. Such a solution of solutes is commonly known as ultrafiltrate and it will, therefore, be referred to as such hereinafter. As described by Dr. Golper, a CAVH system requires the establishment of a blood flow line from an artery of the patient through the filter and back into a vein of the patient. In accordance with CAVH, as blood passes through the filter, the ultrafiltrate is withdrawn from the filter while the blood continues to flow on through the blood flow line to the patient. After being withdrawn from the filter, the ultrafiltrate is passed through a filtrate port for disposal.

It has been recognized that the volume of ultrafiltrate which is withdrawn from the patient is porportional to the amount of solutes which are withdrawn from the patient's blood supply system. Thus, the volume of withdrawn ultrafiltrate directly affects the level of solutes within the patient's blood system.

Without artificial assistance, a CAVH system as just described must depend on the patient's own blood pressure for movement of blood through the system. This can give rise to several problems. For example, at low blood pressures the potential for blood clotting within the filter is increased. Further, the amount of blood being filtered is reduced.

Since the ability to control the volumetric rate of ultrafiltrate withdrawal will establish an accurate and effective CAVH system, various means have been proposed to accomplish this purpose. Typically such means are directly associated with the fluid line connecting the filter with a fluid collection device. One such means is a simple clamp that operates as disclosed in the article: Journal of Critical Care Nurse, July/August 1984, entitled *Continuous Ultrafiltration-A New ICU Procedure for the Treatment of Fluid Overload* by Williams et al. With a clamp in the ultrafiltrate line leading from the filter, the volumetric flow rate can be somewhat controlled to establish a reasonable approximation of the desired volume withdrawn.

It has also been proposed that an IV peristaltic pump be incorporated into the ultrafiltrate line. Such a combination is disclosed in the article *The Practical Technical Aspects of Slow Continuous Ultrafiltration (SCUF) and Continuous Arteriovenous Hemofiltration (CAVH)* by S. Swann et al., as published in Acute Continuous Renal Replacement Therapy, published by Martinus Nijofff, Boston, Dordrecht Lancaster, 1986. A peristaltic pump, however, requires head pressure to maintain its accuracy. Thus, at low patient blood pressure levels, volumetric inaccuracies are encountered. Thus, neither a clamp nor a linear peristaltic pump in the ultrafiltrate line can provide a routinely reliable system. With either device, the system is still dependent upon the patient's own blood pressure for its operation.

In light of the above, there is a need for a device that can be incorporated into a CAVH system which will provide for the accurate, efficient and reliable withdrawal of a predetermined volume of ultrafiltrate while operating within a pressure range which is compatible with the safety and well being of the patient. Also, there is a need for a CAVH system which can properly operate under artificially induced pressure independently of the patient's blood pressure.

The present invention recognizes that such a device can be established by a volumetric pump which is capable of withdrawing precisely established volumes of ultrafiltrate at a predetermined rate. Further, the present invention recognizes that such a system can function independently of the patient's blood pressure. The present invention also recognizes there is a need for an apparatus in the ultrafiltrate line which is capable of proper operation independently of the head pressure within the system. The present invention further recognizes that a system, such as here envisioned, can be used for plasmapheresis as well as CAVH and that this added feature can be accomplished through the proper selection of appropriate filters.

Accordingly, it is an object of the present invention to provide a system for the withdrawal of a predetermined volume of fluid from a patient which is independent of the head pressure in the system. It is another object of the present invention to provide a fluid withdrawal system which accurately and reliably withdraws a predetermined volume of fluid at a preselected volumetric rate. Yet another object of the present invention is to provide a system for the withdrawal of fluids from a patient which is easily set up and maintained. Still antoher object of the present invention is to provide a fluid withdrawal system which is cost effective and efficiently operated.

SUMMARY OF THE INVENTION

A preferred embodiment of the novel system for volumetric withdrawal of fluids from a patient includes a filter assembly which has an arterial port in fluid communication with an artery of the patient. Further, the filter assembly includes a venous port which is in fluid communication with a vein of the patient and a filtrate port which is connected in fluid communication with a volumetric pump.

Operation of the volumetric pump causes ultrafiltrate fluid to be withdrawn from the filter assembly and into the pump chamber at a predetermined rate. Valve means within the pump allows for alternatingly withdrawing ultrafiltrate from the filter and emptying the ultrafiltrate from the pump's fluid chamber into a fluid collection device. Electronic programmable means associated with the pump causes the empty cycle to be done at a rate which is much higher than that for the withdrawal of ultrafiltrate fluid from the patient.

The fluid volumetric withdrawal system may also include fluid sources appropriately attached to the arterial line or the venous line to permit fluid volume bulk replacement for the patient. Further, the system may permit substitution of the hemofilter with a plasmapheresis filter.

The novel features of this invention as well as the invention itself, both as to its organization and operation, will be best understood from the accompanying drawings taken in conjunction with the accompanying description in which similar reference characters refer to similar parts and in which:

DESCRIPTION OF THE PREFERRED EMBODIMENT

Figure 1:
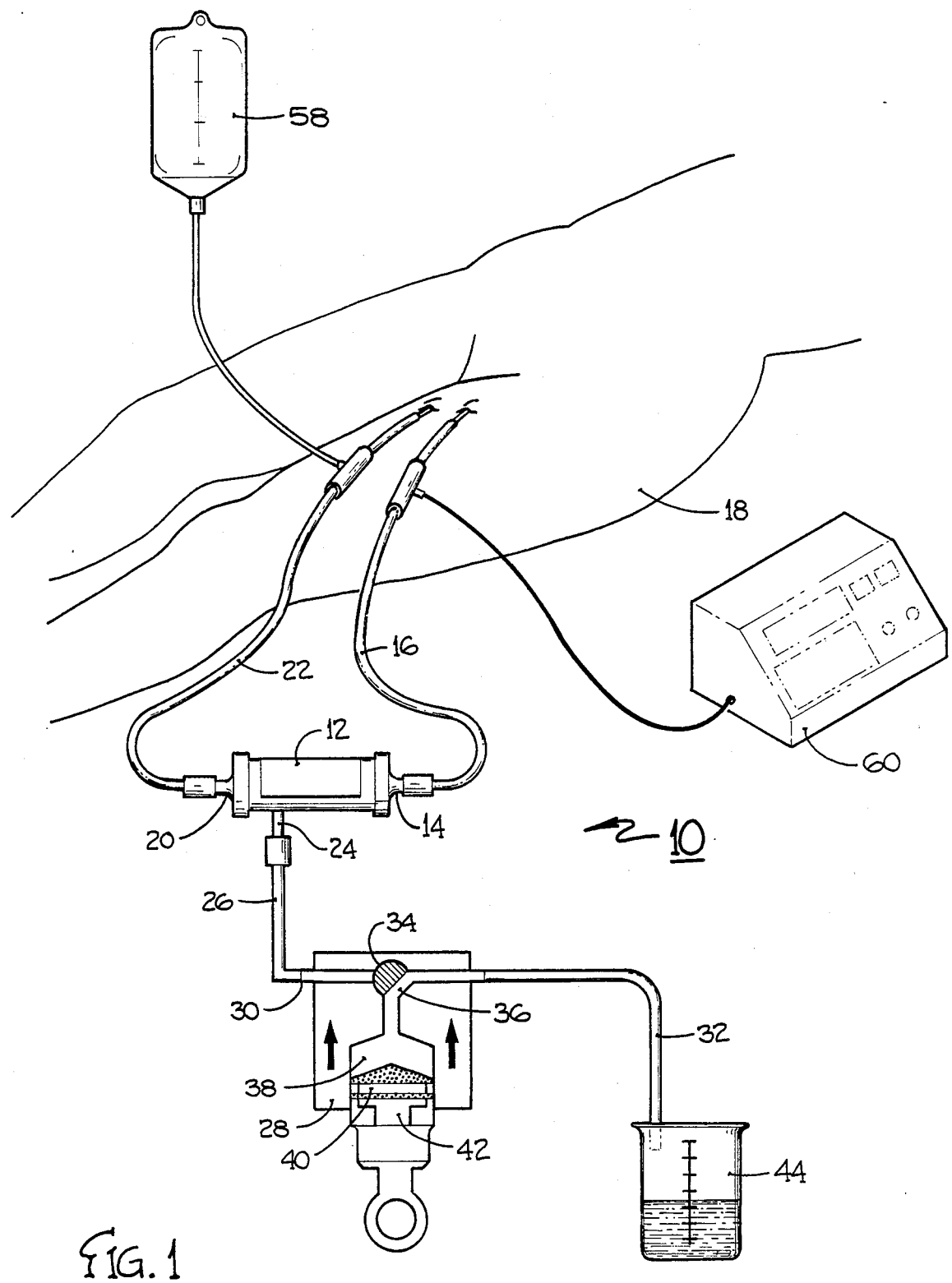
FIG. 1 is a schematic view of the volumetric fluid withdrawal system in an operational environment.

Referring initially to FIG. 1, it can be seen that the fluid volumetric withdrawal system of the present invention, generally designated 10, includes a filter 12. For purposes of the present invention, filter 12 may be either a hemofilter or a plasmapheresis filter depending upon the particular desires and needs of the operator. It will be understood by the skilled artesan that the distinction between a hemofilter and plasmapheresis filter lies in the size of pores which are incorporated into the filtering material. As shown in FIG. 1, filter 12 is formed with an arterial port 14 which is connected in fluid communication with arterial line 16. Arterial line 16 is connected directly from filter 12 into an artery of the patient 18. Thus, fluid coursing through the patient's body 18 enters arterial line 16 and passes therethrough to the filter 12.

Filter 12 also includes a venous port 20 which is connectable in fluid communication with a venous line 22. As shown, venous line 22 is connected directly from filter 12 into a vein of the patient 18. Filter 12 further includes a filtrate port 24 which is connected to a filtrate line 26 that establishes fluid communication between the filter 12 and IV pump 28.

Still referring to FIG. 1, it can be seen that pump 28 is formed with an inlet 30 and an outlet 32. A valve 34 having a passageway 36 formed therethrough is rotatably mounted on pump 28 to alternatingly establish fluid communication between chamber 38 of pump 28 and either inlet 30 or outlet 32. As will be appreciated by the skilled artesan, the operation of system 10 is dependent upon the movement of plunger 40 within chamber 38 as caused by the reciprocal action of piston 42. FIG. 1 also shows that filtrate line 26 is continued from pump 28, through outlet 32, and terminates with its connection to a fluid collection device 44. The exact operation of system 10 is accomplished in a manner to be subsequently described in detail.

Figure 2:
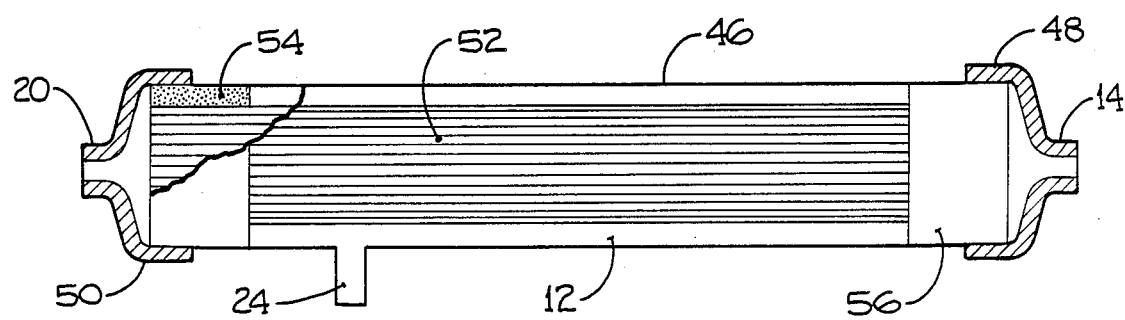
FIG. 2 is a side view of the filter with portions broken away and shown in cross-section for clarity.

Referring now to FIG. 2, a more detailed description of the components included in the filter 12 can be appreciated. As shown in FIG. 2, filter 12 includes a housing 46 which is generally formed as a hollow cylinder. An end cap 48 which includes arterial port 14 covers one end of housing 46. At the end of housing 46, opposite end cap 48, is a similar end cap 50 which includes venous port 20. Contained within housing 46 of filter 12 between end caps 48 and 50 is a fiber bundle 52. It will be appreciated by the skilled artesan that fiber bundle 52 includes a plurality of hollow tubular shaped fibers and that the pore sizes in the walls of the hollow fibers which comprise the fiber bundle 52 can be varied during manufacture. Thus, fiber bundle 52 can be selected with various sieving capabilities depending on the particular use intended for system 10. As shown in FIG. 2, fiber bundle 52 is held within housing 46 by potting compound 54 and potting compound 56 included at the respective ends of fiber bundle 52. A detailed description of a filter such as filter 12 is provided in an article entitled *Mass Transfer and Arterial Venous Hemofiltration* by M. J. Lysaght et al., as published in Arterial Venous Hemofiltration published by Spriger-Verlag, Berlin, Heidelberg 1985.

Returning now to FIG. 1, it can be seen that system 10 can incorporate additional elements. Specifically, in FIG. 1, a fluid source 58 is shown connected in fluid communication with venous line 22. Fluid from source 58 can be infused to patient 18 for the purpose of providing fluid volume bulk replacement. As is well understood by the skilled artesan, fluid volume bulk replacement is necessary in a CAVH system to maintain proper fluid level for the patient. Although fluid source 58 is shown connected to venous line 22 for postdilution of the filtered blood, it is to be understood that a predilution is possible in a system wherein a fluid source (not shown) is connected in fluid communication with arterial line 16. Either configuration is efficacious for the intended purpose. It is also shown in FIG. 1 that a pump 60 may be incorporated into the system to infuse an anticoagulant, such as heparin, for the purpose of preventing blood clotting at filter 12.

OPERATION

In the operation of the present invention, it will be appreciated by reference to FIG. 1, that filter 12 is connected in fluid communication with an artery of patient 18 via arterial line 16. Also filter 12 is connected to a vein of patient 18 via venous line 22. As blood passes through arterial line 16 and into filter 12, it comes into contact with fiber bundle 52. It will be understood by the skilled artesan that as blood passes through fiber bundle 52 that an ultrafiltrate, containing solutes such as creatinine, BUN and potassium, passes through the pores and membranes (not shown) of fiber bundle 52 and collects within housing 46. This ultrafiltrate solution eventually passes out of filter 12 via filtrate port 24. While ultrafiltrate is being collected in the housing 42, the filtered blood continues to pass through fiber bundle 52 and exits from filter 12 via venous port 20 from where it passes through venous line 22 and back to patient 18.

Figure 3:
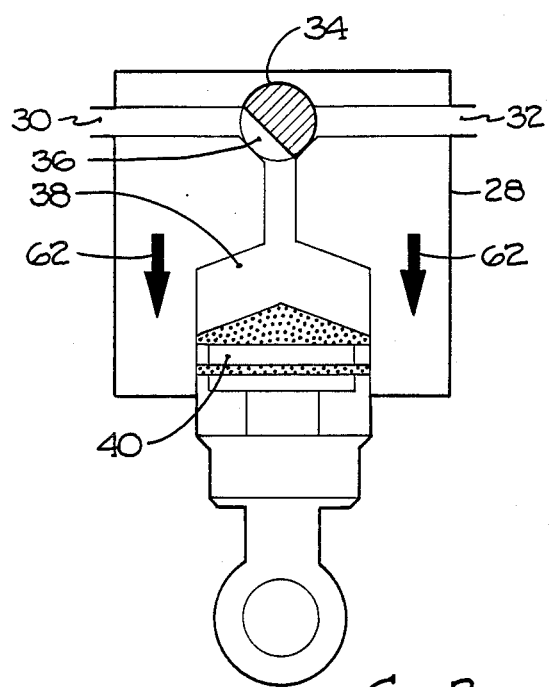
FIG. 3 is a cross-sectional view of the pumping mechanism of a volumetric pump oriented for withdrawing fluids from the filter.
Figure 4:
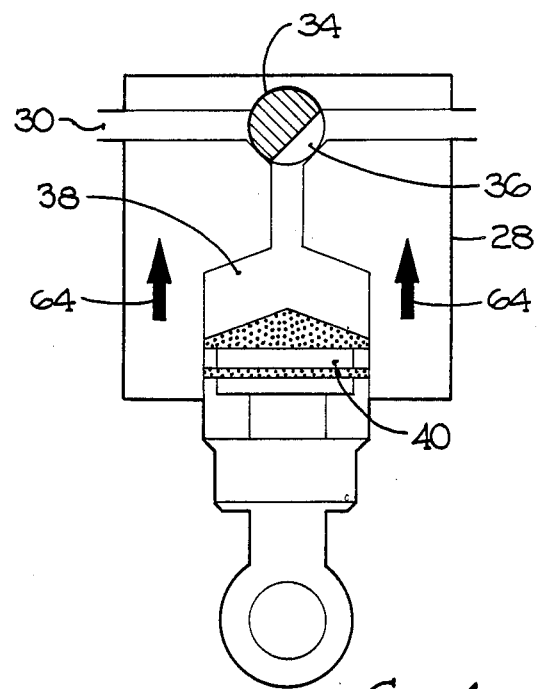
FIG. 4 is a cross-sectional view of the pumping mechanism of a volumetric pump oriented for expelling fluids to a fluid collection device.

The mechanism for evacuating ultrafiltrate from filter 12 can be best seen with reference to FIGS. 3 and 4 where the actual operation of pump 28 can be best understood. In FIG. 3 pump 28 is shown with valve 34 positioned to establish fluid communication between filtrate line 26 and chamber 38. Thus, with valve 34 in this position, as piston 42 is reciprocally moved to displace plunger 40 in a direction indicated by arrows 62, ultrafiltrate will be drawn from filter 12 and into the chamber 38 via inlet 30. Once a predetermined volume of ultrafiltrate has been collected within chamber 38, valve 34 is rotated to a position as shown in FIG. 4. When valve 34 is positioned as shown in FIG. 4, passageway 36 establishes fluid communication between chamber 38 and outlet 32 and an advancement of plunger 40 into chamber 38 by actuation of piston 42 in a direction indicated by arrows 64 causes the ultrafiltrate that had been collected in chamber 38 to be expelled out of outlet 32. In the manner just described, valve 34 can be alternatingly moved between its position in FIG. 3 to its position as shown in FIG. 4 to sequentially draw ultrafiltrate from filter 12 and then expel the collected ultrafiltrate via outlet 32 through a line to fluid collection device 44.

As intended by the present invention, the pump 28 is electronically controlled in a manner which provides for a relatively slow drawing of ultrafiltrate from filter 12. Thus, the filling cycle for chamber 38 is accomplished over a relatively extended period of time. On the other hand, the expulsion of ultrafiltrate from chamber 38 and into fluid collection device 44 is accomplished within a relatively short period of time. This is done to allow for as continuous a withdrawal process of ultrafiltrate from filter 12 as can be possible. It will be understood by the skilled artesan that although the IV infusion pump described in U.S. Pat. No. 3,985,133 to Jenkins is suitable for use with the present invention it must be modified to operate on a cycle which is essentially the reverse of the cycling requirements needed for the proper operation of the system 10. Specifically, under a normally described IV volumetric infusion pump operation, as disclosed in the Jenkins patent, the fill cycle is accomplished in a relatively short period of time and the expulsion or infusion cycle is accomplished over an extended period of time. Again, these cycles must be reversed for the present invention to provide for a slow fill cycle and a rapid empty cycle. Thus, in acccordance with the present invention, this cycling sequence is intended to accomplish a substantially continuous withdrawal of ultrafiltrate from filter 12.

While the particular system for volumetric fluid withdrawal from a patient as herein shown and disclosed in detail is fully capable of obtaining the objects and providing the advantages hereinbefore stated, it is to be understood that it is merely illustrative of the presently preferred embodiment of the invention and that no limitations are intended to the details of construction or design herein shown other than as defined in the appended claims.

I claim:

1. A system for volumetric withdrawal of fluid from a patient which comprises:
    an assembly having a porous filter and formed with a venous port, an arterial port and a filtrate formed with a venous port, an arterial port and a filtrate port;
    a volumetric pump having a fluid chamber of predetermined volume, said chamber having an inlet and an outlet with said inlet connected for fluid communication with said filtrate port to provide a direct effect on the filtering process by said pump and, said pump having a piston slidably received in said chamber to vary the volume of said chamber; and
    control means operatively connected with said piston to alternatingly draw fluid from said filter into said chamber at a predetermined rate compatible with the capacity of said filter and empty fluid from said chamber through said outlet.

2. A system as cited in claim 1 wherein said control means empties fluid from said chamber at a faster rate than said means draws fluid from said assembly.

3. A system as cited in claim 2 further comprising a fluid collection device in fluid communication with said outlet.

4. A system as cited in claim 3 further comprising a venous line having a first end connected in fluidwise communication with said venous port of said filter and a second end adapted for insertion into a vein of a patient.

5. A system as cited in claim 4 further comprising an arterial line having a first end connected in fluidwise communication with said venous port of said filter and a second end adapted for insertion into an artery of a patient.

6. A system as cited in claim 5 further comprising a fluid source in fluid communication with said venous line.

7. A system as cited in claim 5 further comprising a fluid source in fluid communication with said arterial line.

8. A system as cited in claim 1 wherein said assembly comprises a hemofilter.

9. A system as cited in claim 1 wherein said assembly comprises a plasmapheresis filter.

10. An apparatus useful for continuous arteriovenous hemofiltration which comprises:
    a porous fiber bundle;
    a filter housing formed as a hollow cylinder for receiving said fiber bundle therein, said housing having an arterial port, a venous port and a filtrate port;
    a pump having an inlet and an outlet and having a chamber in fluid communication with said inlet and said outlet;

a connector fluid line connecting said filtrate port into fluid communication with said inlet;

a piston operatively associated with said pump and positioned thereon for reciprocal movement in said chamber between a first position and a second position for varying the effective volume of said chamber according to the position of said piston in said chamber;

a valve operatively associated with said chamber to alternatingly block fluid communication between said inlet and said chamber or between said outlet and said chamber;

means associated with said pump to synchronize operation of said valve with said piston to draw fluid from said filter housing through said connecting fluid line into said chamber and to expel fluid from said chamber through said outlet; and means associated with said pump to alternatingly provide for controlled drawing of fluid into said chamber at a relatively slow volumetric flow rate and for relatively rapid expulsion of fluid from said chamber.

11. A method for setting up a system and drawing fluid from a patient at a predetermined volumetric rate for continuous arteriovenous hemofiltration which comprises the steps of:

(a) obtaining a filter assembly for holding a porous filter, said assembly having a venous port, an arterial port and a filtrate port;

(b) connecting a venous line between a vein of the patient and said venous port and an arterial line between an artery of the patient and said arterial port to establish a blood flow route through said filter;

(c) engaging a volumetric pump with said filtrate port of said filter assembly to provide a direct effect on the filtering process by said pump, said pump having a fluid chamber and a piston slidably disposed in said chamber to vary the volume thereof, said chamber formed with an inlet and an outlet with said inlet engaged in fluid communication with said filtrate port; and (d) operating a control means connected with said pump to alternatingly draw fluid from said filter into said chamber at a predetermined rate and emptying fluid from said chamber through said outlet.

* * * * *

UNITED STATES PATENT AND TRADEMARK OFFICE
CERTIFICATE OF CORRECTION

PATENT NO. : 4,767,399

DATED : August 30, 1988

INVENTOR(S) : Stephen J. Bollish

It is certified that error appears in the above-identified patent and that said Letters Patent is hereby corrected as shown below:

On column 6, line 16 delete the word "formed" after the word "filtrate" and on line 17 delete "with a venous port, an arterial port and a filtrate".

Signed and Sealed this

Twenty-fifth Day of April, 1989

Attest:

DONALD J. QUIGG

Attesting Officer

Commissioner of Patents and Trademarks